United States Patent
Bauer

(10) Patent No.: US 7,001,441 B2
(45) Date of Patent: Feb. 21, 2006

(54) STERILIZATION CONTAINER FILTER SYSTEM

(75) Inventor: Witold Bauer, Westlake, OH (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 10/872,230

(22) Filed: Jun. 18, 2004

(65) Prior Publication Data

US 2004/0222116 A1    Nov. 11, 2004

Related U.S. Application Data

(62) Division of application No. 10/199,447, filed on Jul. 18, 2002.

(51) Int. Cl.
*A61L 2/20* (2006.01)

(52) U.S. Cl. .......................... 55/385.4; 422/22; 422/28; 422/297; 422/300; 422/310; 422/366; 206/438; 220/315; 220/371; 220/372; 220/367.1

(58) Field of Classification Search ............... 55/385.4; 422/22, 28, 297, 300, 310, 366; 206/438–363; 220/315, 371, 372, 367.1
See application file for complete search history.

(56) References Cited

U.S. PATENT DOCUMENTS

| | | |
|---|---|---|
| 2,384,398 A | 9/1945 | Raven |
| 3,252,580 A | 5/1966 | Getzin |
| 3,259,411 A | 7/1966 | Griffiths |
| 3,957,469 A | 5/1976 | Nebash |
| 3,966,439 A | 6/1976 | Vennos |
| 4,194,622 A | 3/1980 | Lewis |
| 4,244,920 A | 1/1981 | Manschot et al. |
| 4,318,557 A | 3/1982 | Bourne et al. |
| 4,331,257 A | 5/1982 | Taschner |
| 4,358,908 A | 11/1982 | Song |
| 4,372,921 A | 2/1983 | Sanderson et al. |
| 4,382,808 A | 5/1983 | Van Wormer, Jr. et al. |
| 4,416,417 A | 11/1983 | Sanderson et al. |
| 4,481,797 A | 11/1984 | Milo |
| 4,487,606 A | 12/1984 | Leviton et al. |
| 4,510,119 A | 4/1985 | Hevey |
| 4,512,498 A | 4/1985 | Leibinger |
| 4,514,361 A | 4/1985 | Hirsch |
| 4,551,311 A | 11/1985 | Lorenz |

(Continued)

FOREIGN PATENT DOCUMENTS

AU    202334    7/1956

(Continued)

*Primary Examiner*—Minh-Chau T. Pham
(74) *Attorney, Agent, or Firm*—Andrew G. Rozycki

(57) ABSTRACT

The invention described herein relates to a filter system for sterilization containers which secures a gas permeable filter onto a vented portion of the container. The filter system of the invention includes a locking mechanism that is comfortable and easy to use, and that requires a simple sliding movement of the users hand to lock and unlock the filter system components in place. The invention further includes a filter system structured such that the openings of the filter system plates permit transport of air across the filter while at the same time the openings are arranged to reduce or prevent undesirable physical perforation of the filter. By virtue of its structure, the need for particular rotational positioning of filter components in relation to one another is significantly reduced. The filter system of the invention also reduces or eliminates the need for perimeter gaskets. The invention is useful in a variety of medical applications wherein sterilization of medical devices and instruments is associated with a surgical treatment or procedure.

1 Claim, 6 Drawing Sheets

U.S. PATENT DOCUMENTS

| | | | |
|---|---|---|---|
| 4,617,178 A | 10/1986 | Nichols | |
| 4,666,479 A * | 5/1987 | Shoji | 55/385.4 |
| 4,716,025 A | 12/1987 | Nichols | |
| 4,728,504 A | 3/1988 | Nichols | |
| 4,783,321 A * | 11/1988 | Spence | 422/300 |
| 5,098,676 A | 3/1992 | Brooks, Jr. | |
| 5,176,884 A | 1/1993 | Taschner et al. | |
| 5,183,643 A | 2/1993 | Nichols | |
| 5,324,489 A | 6/1994 | Nichols et al. | |
| 5,328,661 A | 7/1994 | Taschner | |
| 5,372,787 A | 12/1994 | Ritter | |
| 5,474,738 A | 12/1995 | Nichols | |
| 5,524,755 A | 6/1996 | Deeds | |
| D374,936 S | 10/1996 | Jakab | |
| 5,628,970 A | 5/1997 | Basile et al. | |
| 5,687,885 A | 11/1997 | Turk et al. | |
| 5,725,830 A | 3/1998 | Taschner | |
| 5,732,821 A | 3/1998 | Stone et al. | |
| 5,968,459 A | 10/1999 | Nalepa et al. | |
| 5,971,180 A | 10/1999 | Wu | |
| 6,065,631 A | 5/2000 | Oberhofer et al. | |
| 6,077,485 A * | 6/2000 | Baker | 422/300 |
| 6,161,716 A | 12/2000 | Oberhofer et al. | |
| 6,589,477 B1 * | 7/2003 | Frieze et al. | 422/22 |
| 2003/0180807 A1 * | 9/2003 | Hess et al. | 435/7.1 |

FOREIGN PATENT DOCUMENTS

| | | |
|---|---|---|
| DE | 908407 | 10/1962 |
| FR | 2375869 | 7/1978 |
| JP | 05132040 | 5/1993 |

* cited by examiner

STERILIZATION CONTAINER FILTER SYSTEM

RELATED APPLICATION DATA

This application is a divisional of U.S. patent application Ser. No. 10/199,447 filed Jul. 18, 2002, now pending.

FIELD OF THE INVENTION

The invention relates to the field of sterilization containers used for the sterilization of medical devices. In particular, the invention pertains to a filter retention system used with sterilization containers.

BACKGROUND OF THE INVENTION

Prior to medical and surgical procedures or treatments, sterilization of medical devices and instruments prior to their use is necessary to reduce the risk of infection from microbes on such equipment. Various sterilization techniques are utilized in the medical field, such as irradiation of equipment, treatment using antimicrobial solutions, and temperature sterilization techniques. One of the most commonly employed techniques is sterilization using an autoclave, which involves placement of the equipment to be sterilized within a chamber which is subsequently heated to a temperature and for a time period sufficient to kill microbial agents which can be present on the equipment.

Sterilization containers are sometimes used to house surgical instruments and other devices to be sterilized. Typical sterilization containers are constructed of a lid and base portion, and a vent portion located on the lid, base or both. The vent portion permits the movement of gases to accommodate the changes in pressure created by increasing or decreasing temperatures of the internal and external environments of the container. In order to prevent contamination by the handling and storage of sterilization containers, filters can be positioned in relation to the vent portion to permit the transport of gases but reduce or prevent the transport of microbes.

Filter systems for sterilization containers have been developed. Typical filter systems include a filter retainer and an associated locking mechanism to secure the filter in place relative to the vent portion of the container. Such a filter retention system is described in Nalepa et al. U.S. Pat. No. 5,968,459, which describes a filter retention system including a rotating locking plate which secures a filter retaining plate and filter to a sterilization container having vent openings. One drawback of this system, however, is that it requires a turning or pivoting movement by the user's hand, and does not provide a penetration resistant structure to protect the filter from piercing. Another filter system is described in Spence U.S. Pat. No. 4,783,321, which discloses a penetration resistant filter retaining system having an upper retainer disc and lower retainer disc. This system, however, requires precise positioning of the retainer discs in relation to one another and the vent openings, and does not contain a single, centrally located locking mechanism.

There is a need for improved filter systems useful for sterilization containers that facilitate the filter retention function of the container while maintaining the properties required for sterilization processes. There is a further need for filter systems which secure a filter onto a sterilization container, protect the filter from damage or unintended movement, and reduce the likelihood of contamination both during and following sterilization. There is yet a further need for filter systems which are ergonomic and afford the user a comfortable assembly and preparation, especially when such activities are repeated tasks.

SUMMARY OF THE INVENTION

The invention provides a filter system for sterilization containers comprising a locking mechanism that is comfortable and easy to use and that requires a simple sliding movement of the users hand to lock and unlock the filter. It has further been discovered that a filter system can be constructed to reduce or eliminate the need for precise positioning of filter components in relation to one another by the user to prevent the likelihood of physical puncture of the filter while at the same time permitting the unobstructed transport of air across the filter layer. The filter system of the invention is also relatively easy to manufacture. The filter system of the invention also does not require the use of gaskets circumscribing the perimeter of the system. The invention is particularly useful in a variety of medical applications wherein sterilization of medical devices and instruments is needed for a surgical treatment or procedure.

The invention provides a filter system for a sterilization container having a lid, base and vented portion, said filter system comprising:

a first filter retention plate adapted for positioning and retaining a filter over a vented portion of said container;

a second filter protective plate adapted for positioning between said filter and said vented portion of said container;

wherein each of said first plate, second plate, and filter is adapted to align with and be positioned in relation to a central pin extending outward from said vented portion of said container; and a locking mechanism adapted to secure said first plate, second plate and filter onto said container, said locking mechanism comprising a locking plate adapted for linear sliding movement in a direction substantially parallel to the surface of said first plate.

The invention further provides a locking mechanism for a sterilization container filter system having a vented portion, said locking mechanism comprising:

a first filter retention plate;

a locking plate having an elongate opening and attached to the upper surface of said first filter retention plate, and adapted for linear sliding movement in a direction substantially parallel to the surface of said plate;

wherein said locking plate is adapted to cooperate with a central pin extending outward from a vented portion of the sterilization container; and wherein linear sliding movement of said locking plate increases the vertical compressive force between the filter system components.

The invention also provides a filter system for a sterilization container having a vented portion comprising a plurality of openings, said filter system comprising:

a first filter retention plate comprising a plurality of openings;

a second protective plate comprising a plurality of openings;

wherein said first filter retention plate and second protective plate are adapted to accommodate and retain a gas-permeable filter therebetween; and wherein each of said first retention plate and second protective plate are structured so that the openings thereof and said openings of said vented portion are arranged to permit substantially unobstructed movement of air across said filter while forming a barrier to transverse physical perforation of said filter, said openings maintaining such barrier irrespective of rotational positioning of said plates relative to a central axis.

The invention further provides a filter system for a sterilization container having a vented portion comprising a plurality of openings, said filter system comprising:

a first filter retention plate comprising a plurality of openings;

a second protective plate comprising a plurality of openings;

wherein said first filter retention plate and second protective plate are adapted to accommodate and retain a gas-permeable filter therebetween; and wherein each of said first retention plate and second protective plate are structured so that the openings thereof and said openings of said vented portion are arranged to permit substantially unobstructed movement of gases across said filter while forming a barrier to transverse physical perforation of said filter, said openings maintaining such barrier irrespective of rotational positioning of said plates relative to a central axis.

DETAILED DESCRIPTION OF THE INVENTION

Figure 1:
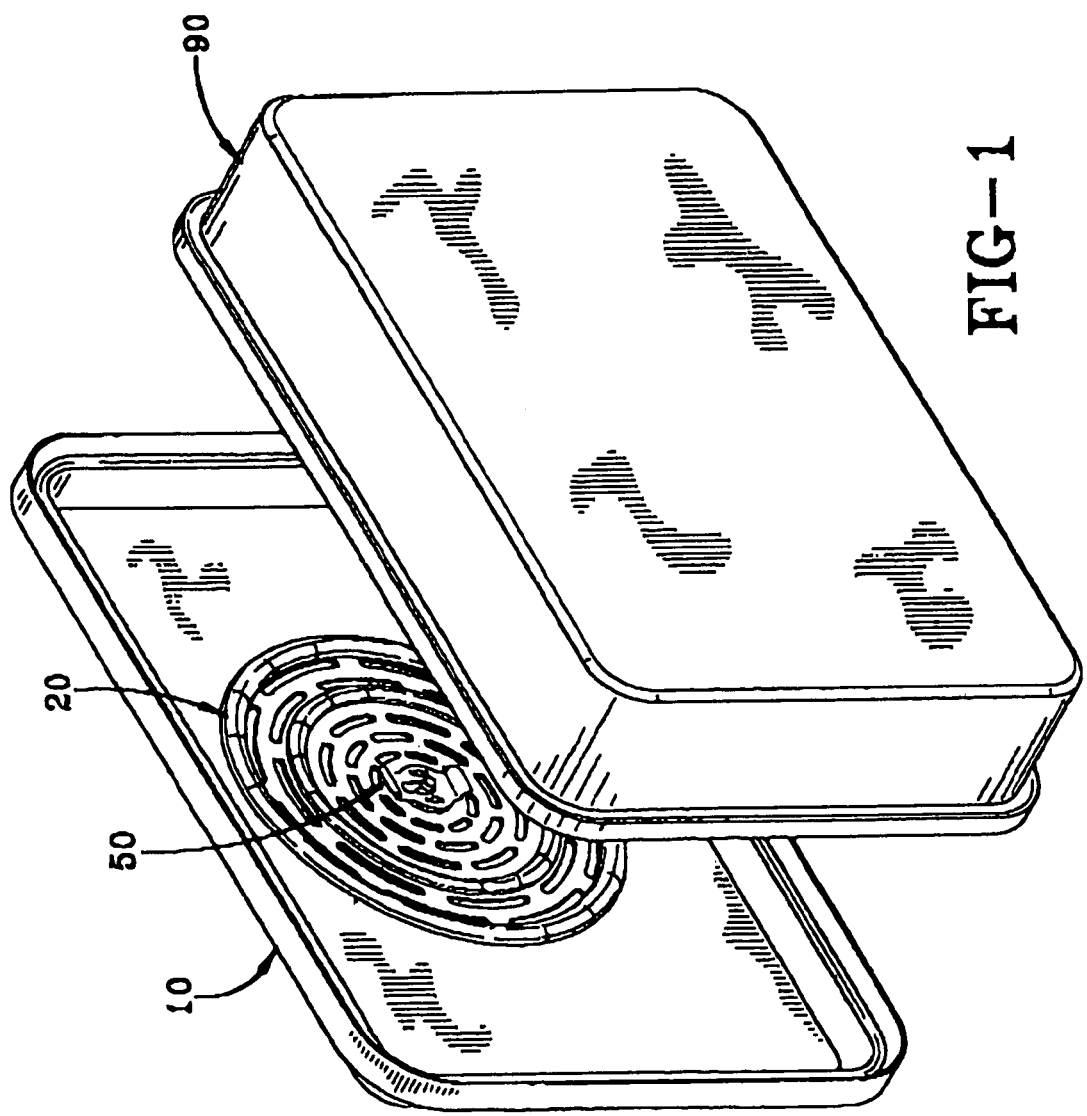
FIG. 1 is an angled side view of a sterilization container showing the lid and filter assembly attached thereto and the base portion separated from the lid according to one embodiment of the invention.

As used herein, the term "plate" is meant to refer to a component having a substantially planar construction. The term is not intended to imply a limitation as to a particular perimeter configuration, such as a circular, disc-like shape.

In general, the filter system of the invention is designed for use as a component in a sterilization container. Suitable sterilization containers for use with the filter system of the invention can include a basic construction of a lid and base portion, wherein at least one of either the lid, the base, or both, contains a vented portion. For purposes of illustration, the invention is depicted in the drawings as having the filter system located on the lid, the lid containing the vented portion of the container. In a further embodiment, a sterilization container can be constructed to have more than one vented opening and corresponding filter system therewith. The filter system of the invention performs the overall function of securing a gas permeable filter over a vented portion of a sterilization container and maintaining the position of the filter to create a separate internal and external environment relative to the container throughout the sterilization process. The filter thus functions to permit the transport of air/gas across the filter membrane, while reducing or preventing migration of microbes therethrough.

Figure 2:
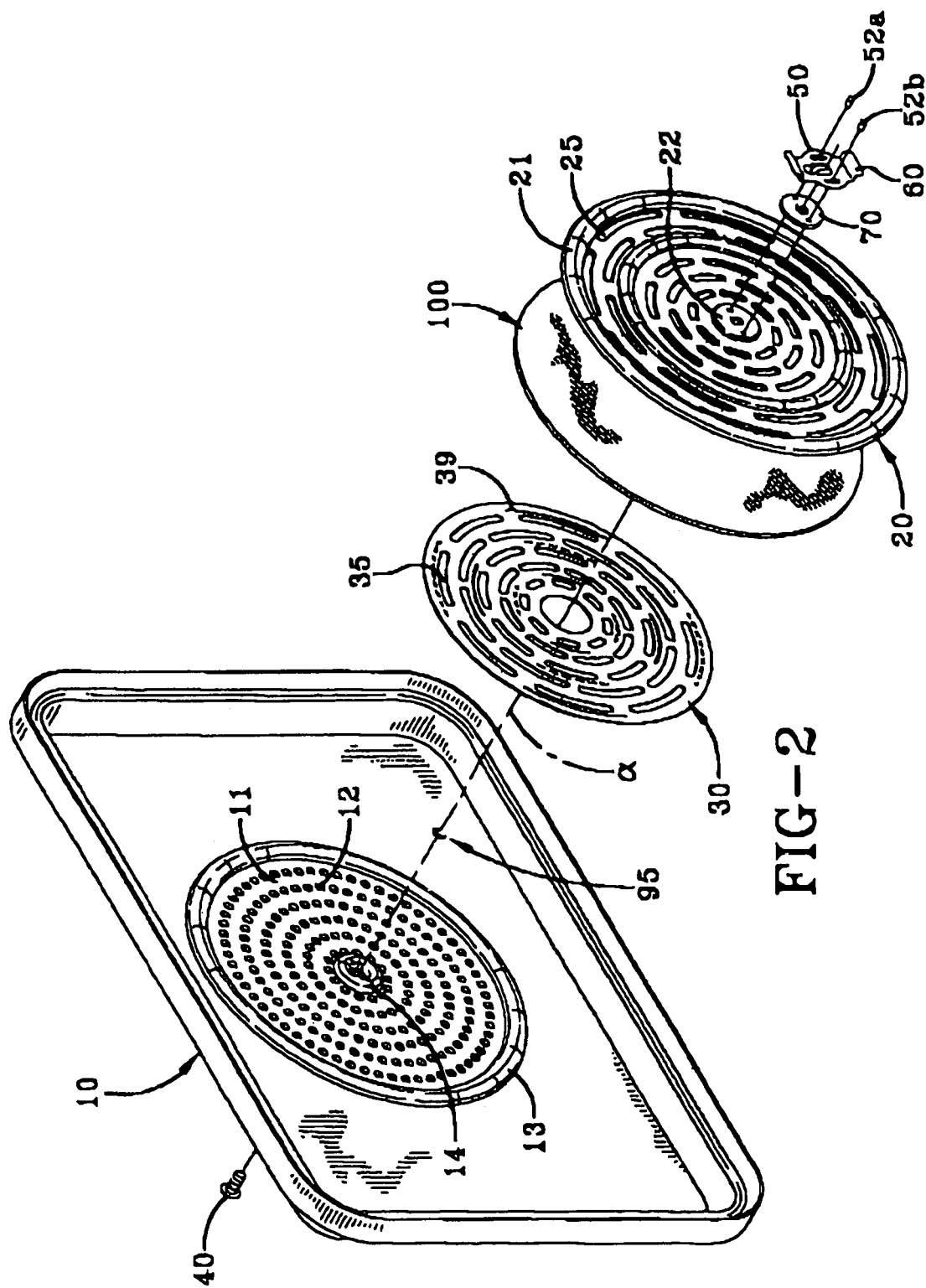
FIG. 2 is an exploded view of a sterilization container lid with the filter system components separated and including a filter according to one embodiment of the invention.

Referring now to FIG. 2, the filter system components are shown in association with a sterilization container lid 10. The vented portion 11 contains a plurality of vent openings 12 through the lid 10, and the vent openings 12 are arranged to cooperate with a gas-permeable filter 100 and the filter plates such that when the filter system is completely assembled, all vent openings 12 of the container are covered by the filter. Referring now to FIG. 1, the lid of the sterilization container can be secured onto the base portion 90 by a securing mechanism (not shown), such as a latch. The securing mechanism can be structured to create a seal which prevents air flow at the lid-base juncture around the perimeter of the lid. One or both of the contacting surfaces of the lid and base can contain a gasket or seal completely circumscribing the contacting surface(s).

The basic sterilization container components can be composed of any medical grade material which can be used in autoclave sterilization. Typically, the basic sterilization container components are composed of stainless steel. Secondary components such as gaskets, washers, and the like, can be composed of any suitable sterilizable material, such as plastic. The various components of the invention can be manufactured using techniques, machining equipment, and materials readily available in the sterilization container manufacturing field.

Figure 7:
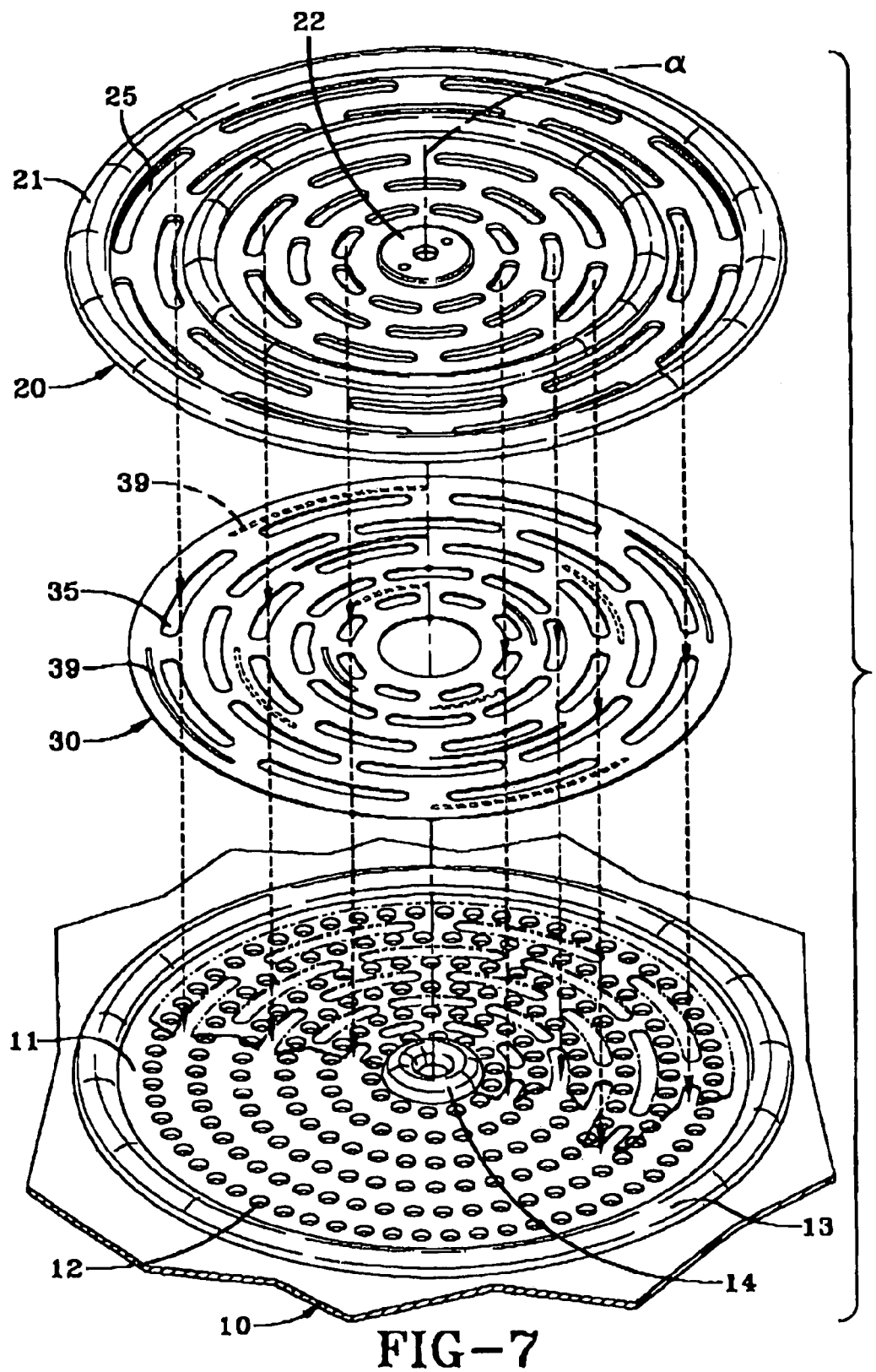
FIG. 7 is an exploded angled side view of the filter system showing separated components and alignment of openings thereof, including a transparent cut-away view of the second protective plate positioned on a cut-away vented portion of the lid, in accordance with one embodiment of the invention.
Figure 8:
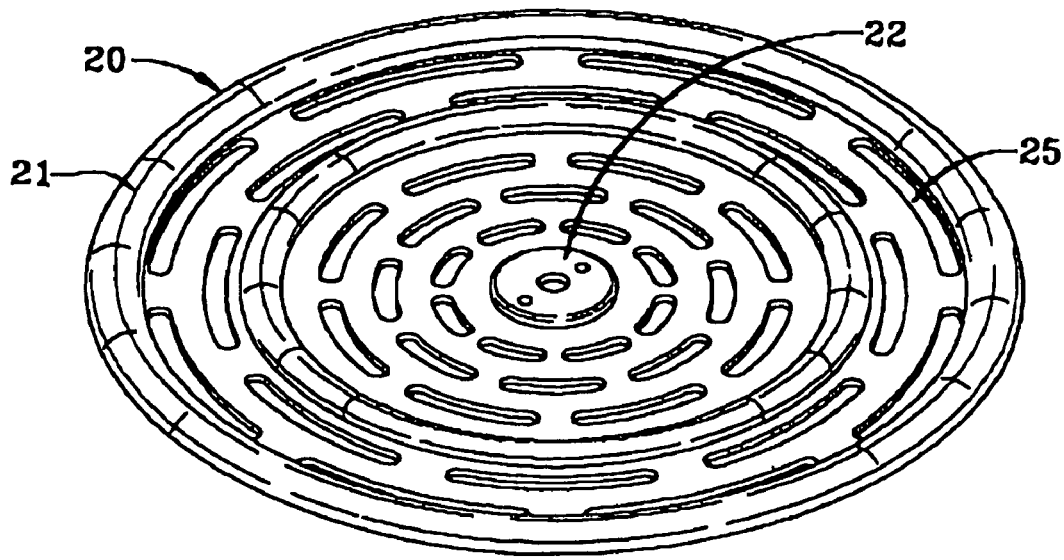
FIG. 8 is an angled top view of a first filter retention plate in accordance with one embodiment of the invention.
Figure 9:
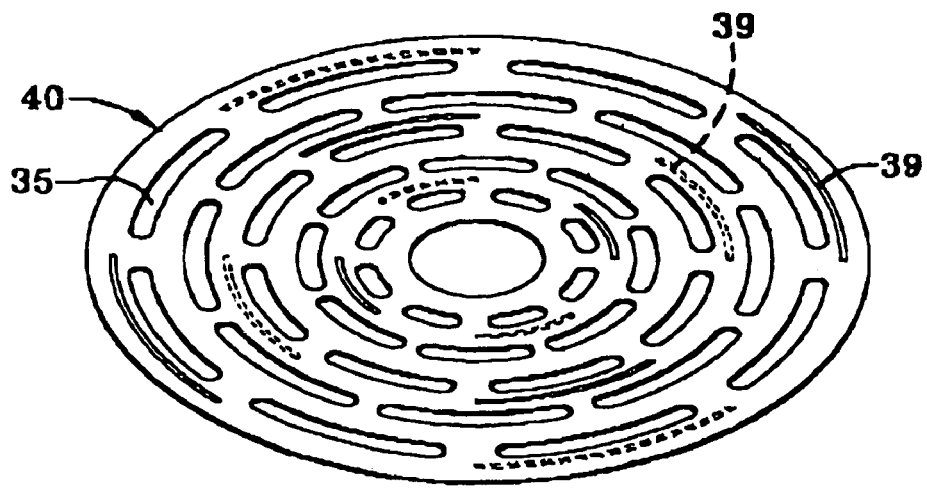
FIG. 9 is an angled top view of a second protective plate in accordance with one embodiment of the invention.

By virtue of its structure, however, the filter system of the invention eliminates the need for gasket components between the plate components. Referring now to FIGS. 2 and 7, the outer boundary of the vented portion 11 of the lid 10 comprises a contiguous raised ring-like perimeter 13 circumscribing the entire vented portion 11. The area immediately surrounding the center of the vented portion 11 also contains a contiguous central raised ring 14. Referring now to FIGS. 2, 3A, 3B and 8, the periphery of the first filter retention plate 20 comprises a contiguous raised rim 21 which is structured to coordinate with the raised perimeter 13 surrounding the vented portion 1. Accordingly, when the filter system is assembled and locked, a gasket-like seal is formed by the superimposing of the first filter retention plate rim 21 and the perimeter 13 at the vented portion 11 of the lid 10. Referring now to FIGS. 2 and 9, the second protective plate 30 is held in place by the central raised ring 14 of the vented portion 11. The central raised ring 14 of the vented portion 11 also cooperates with a corresponding central raised portion 22 on the first retention plate 20 which together also form a gasket-like seal.

The basic filter system components of the invention are shown in FIG. 2. The filter system generally comprises a first filter retention plate 20 and a second filter protective plate 30 which align in cooperation with a central pin 40 extending outward from the vented portion 11 of the container. The first filter retention plate 20 is adapted for positioning and retaining a filter 100 over the second protective plate 30, which in turn is positioned to cover the vented portion 11 of the container. Thus, the second filter protective plate 30 is adapted to be positioned between the filter 100 and the vented portion 11 of the container. Each of the first retention plate 20, second protective plate 30, and filter 100 is sized to align overall in relation to a central axis (designated by the symbol "α") and also to be in alignment with the central pin 40 extending outward from said vented portion 11 of the container.

Locking Mechanism

Figure 3A:
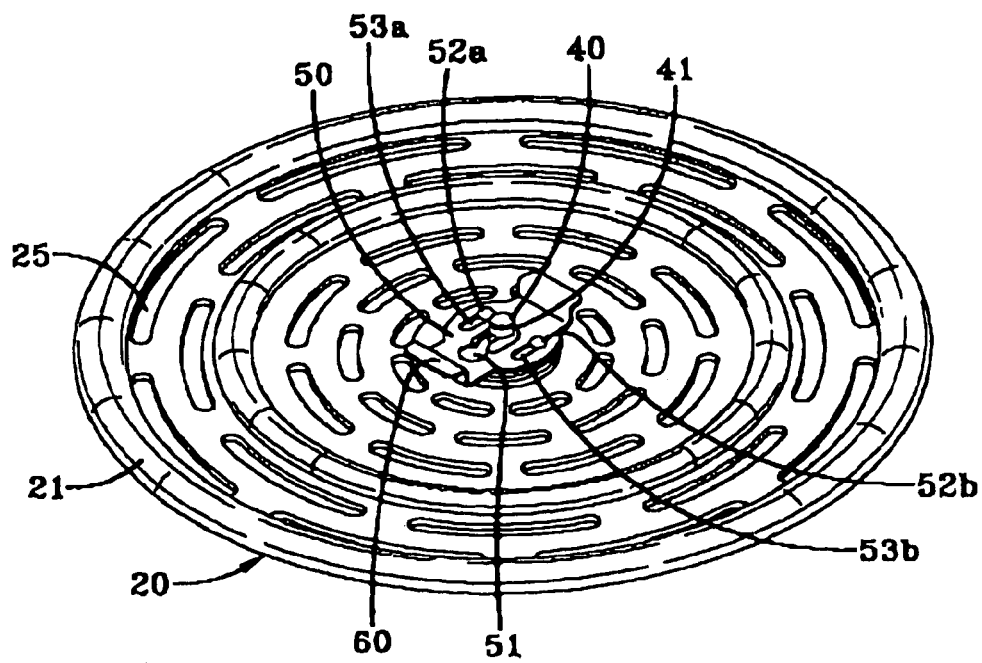
FIG. 3A is an angled side view of the top of the retention plate showing the locking mechanism in the locked position according to one embodiment of the invention.
Figure 3B:
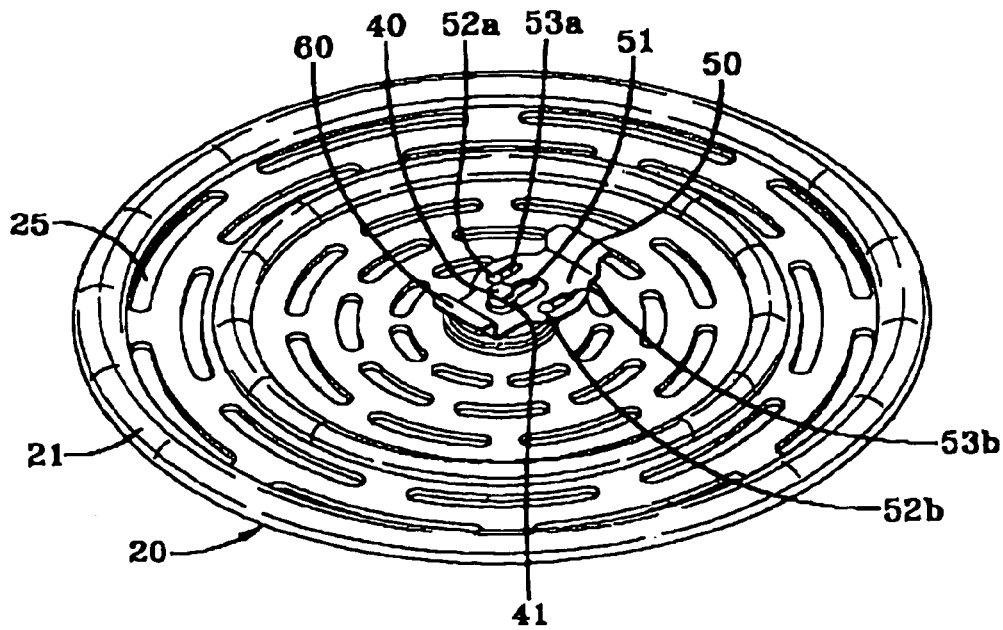
FIG. 3B is an angled side view of the top of the retention plate showing the locking mechanism in the unlocked position according to one embodiment of the invention.

The filter system of the invention further comprises a locking mechanism adapted to secure said first retention plate 20, filter, and second protective plate 30 onto the container. Referring now to FIGS. 3A, 3B, 4, 5 and 6, the locking mechanism comprises a locking plate 50 adapted for bi-directional linear sliding movement in a manner substantially parallel to the planar surfaces of the plates. The locking plate 50 is thus positioned substantially perpendicular relative to the longitudinal central axis α (see FIGS. 2 and 7) of the central pin 40 (as shown in FIGS. 2, 3A and 3B).

Figure 4:
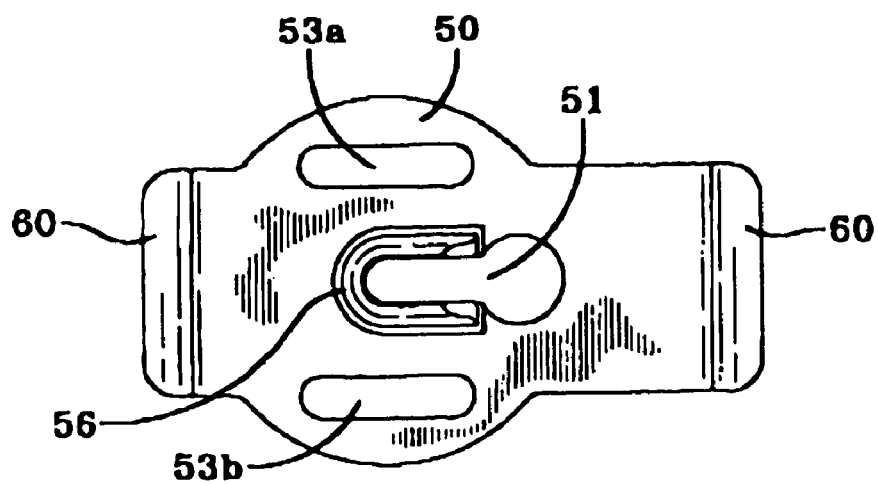
FIG. 4 is a top view of the locking plate component of the locking mechanism according to one embodiment of the invention.
Figure 5:
FIG. 5 is a side view of the locking plate component of the locking mechanism according to one embodiment of the invention.
Figure 6:
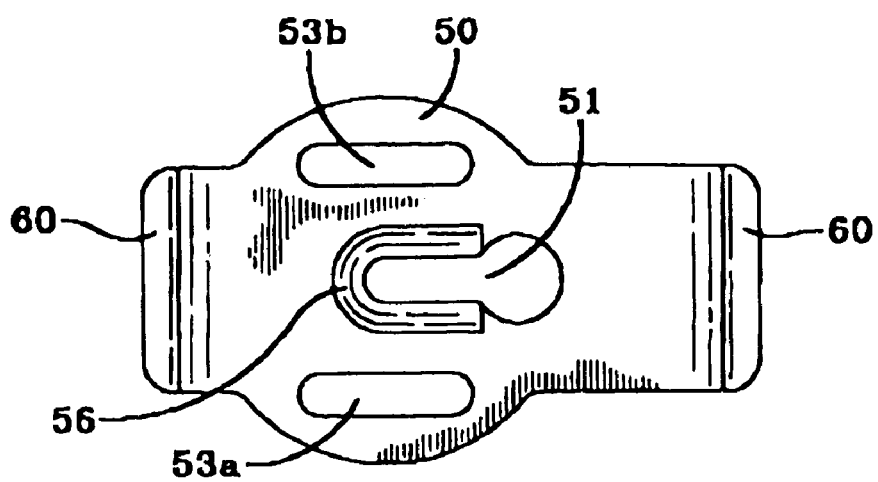
FIG. 6 is a bottom view of the locking plate component of the locking mechanism according to one embodiment of the invention.
Figure 10:
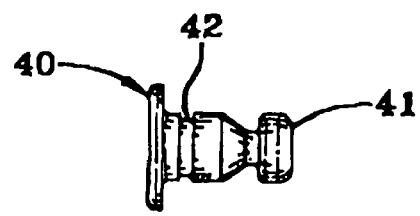
FIG. 10 is a side view of the central locking pin according to one embodiment of the invention.

Referring now to FIGS. 4, 5 and 6, the locking plate comprises an elongate central opening 51 adapted to accommodate a portion of the central pin 40 therethrough. In one embodiment and as seen in FIG. 10, the top of the central pin 40 is widened or tapered to form a "head" 41, the cross-sectional diameter of which is larger than the medial region of the central pin 40. Again referring to FIGS. 4 and 6, one end of the elongate central opening 51 is slightly wider than the other to exclusively accommodate the head 41 of the central pin 40, and the remainder of the elongate central opening 51 is relatively narrower to prevent vertical separation of the central pin 40 from the locking plate 50 by "trapping" the locking plate 50 between the head 41 of the central pin 40 and the upper surface of the first retention plate 20.

To further stabilize the operation of the locking mechanism, the locking mechanism can further comprise stabilization means. In one embodiment, stabilization means can include at least one additional pin-and-slot structure. As can be seen in FIGS. 2, 3A and 3B, the first filter retention plate 20 further comprises at least one guide pin, preferably two guide pins, 52a and 52b respectively, which are adapted to cooperate with at least one corresponding elongate guide opening (illustrated as two elongate guide openings 53a and 53b respectively) in the locking plate 50. Accordingly, undesired rotational or pivoting movement of the locking plate relative to the first retention plate is reduced or eliminated by the stabilization means.

A variety of stabilization means can be used in accordance with the invention. Examples of suitable stabilization means include, but are not limited to, interfitting brackets, toe-in-slot structures, nub-and-groove structures, and the like.

The locking plate 50 can further comprise at least one sliding tab 60 to facilitate manual operation of the locking mechanism 50. The user can easily lock and unlock the locking mechanism by a simple linear sliding movement of the fingers and hand positioned on the sliding tab 60. FIGS. 3A and 3B together illustrate the locked and unlocked positions, respectively, of the locking mechanism. Generally, one of the advantages of the structure of the locking mechanism of the invention is its ease of use. In other words, the locking and unlocking of the locking mechanism does not require awkward, turning or contorting hand movements to operate.

Once the filter system components are stacked and aligned with the central pin 40, the movement of the locking mechanism from the unlocked to the locked positions increases the vertical compressive force between the components. Referring now to FIGS. 4, 5 and 6, one embodiment of such a locking mechanism structure is shown. The region of the locking plate 50 immediately adjacent to each narrower side of the elongate central opening 51 comprises an elevated ramp 56 adapted to interact with the head 41 of the central pin 40. This interaction "traps" the locking plate 50 between the underside of the head 41 and the upper surface of the first retention plate 20 and increases the vertical pressure between the filter system components.

The locking mechanism of the invention can further comprise an intermediate plate 70 (see FIG. 2) to be positioned between the underside of the locking plate 50 and the upper surface of the first retention plate 20. The intermediate plate 70 is preferably composed of a sterilizable resilient material, such as plastic. The intermediate plate 70 functions to place a less rigid material between the rigid components in order to better slide the rigid components together.

The central pin 40 can be permanently fixed to the center of the vent opening 11 of the container using a self-locking retaining ring 95, for example, which can engage central pin recess 42 (see FIG. 10). The locking plate 50 can be permanently but movably attached to the first retention plate 20, positioned to accommodate the central pin 40 through the elongate central opening 51 of the locking plate 50. The guide pin(s) 52a and 52b can be permanently attached to the first retention plate 20. When two guide pins are used, they are preferably located on opposing sides of the elongate central opening 51. The top end of each guide pin can have a head which is wider than the remainder of the guide pin to prevent inadvertent vertical separation of the locking plate 50 from the first retention plate 20.

Filter System Opening Configuration

Another inventive aspect of the filter system of the invention is the structural relationship among the openings of the filter system components. The structure, arrangement and orientation of the openings of each are illustrated in FIG. 7. The vent openings 12, first retention plate openings 25 and second protective plate openings 35, by virtue of their structure and arrangement, are arranged such that when a filter (see FIG. 2) is placed within the filter system, the plates permit substantially unobstructed movement of gases through from the containment interior to the exterior environment while at the same time permitting a physical barrier resistant to unintentional transverse penetration of the filter. Protection of the structural integrity of the filter is an important aspect of the invention, since rupturing the filter jeopardizes the biological containment of the interior environment, thereby compromising sterility of the components placed within the container.

Furthermore, the filter system components are constructed such that this functionality of the opening arrangement is maintained irrespective of the rotational positioning (relative to the central axis α) of the first plate 20 relative to the second plate 30, as well as the relative positioning thereof with respect to the vent openings 12 on the container. In a preferred embodiment, the openings on both the first retention plate and second protective plate are elongate and arcuate, and coordinate to intermittently overlap one another such that at any give position relative to the central axis, an unobstructed opening between the two plates is formed. The region of the vent portion 11 between the vent openings 12 functions as the barrier to transverse physical penetration which would otherwise permit perforation of the filter at the vent opening locations.

At any given rotational position of the first retention plate 20 and second protective plate 30 relative to the container vent openings 12, air exiting the container which passes outward through the vent opening 12 (by virtue, for example, of the pressure created during sterilization temperatures) is diverted in a lateral direction by the solid portion of the second protective plate 30 until it reaches an opening of the second protective plate 30.

Referring now to FIGS. 7 and 9, both the upper and lower surfaces of the second protective plate 30 contain intermittent ridges 39, illustrated as having an arcuate shape, which function to maintain a slight space between the first retention plate 20 and the planar surface of the second protective plate 30 with the filter (not shown) between, as well as a slight space between the second protective plate and the planar surface of the vented portion 11 of the container. Although depicted as arcs, a variety of other shapes and sizes of intermittent ridges can be used provided they accomplish the slight spacing between the plates and surfaces as described.

Again referring to FIG. 7, the gases passing through the second protective plate openings 35 then passes through the filter (not shown). The air continues to exit through the first retention plate openings 25 and exits into the external environment.

The first retention plate openings 25 and the second protective plate openings 35 are configured and dimensioned to provide overlapping regions at multiple locations with the filter inbetween. Thus, another advantage of the invention afforded to the user is that precise or specific positioning of the filter system components, aside from alignment over a central axis, is not necessary. The filter system performs its function(s) irrespective of the rotational alignment of the plates and vented portion of the container. Accordingly, the use and operation of the sterilization container is substantially simplified.

In one example of using the invention, a sterilization container lid is separated from the container base and the filter system components are disassembled—namely, the filter plates are removed from the vent portion of the lid. When the user is ready to seal the contents of the container to be sterilized, the user first places the second protective plate over the vented portion of the container. Then, the filter is placed over the second protective plate, followed by the first retention plate with the locking plate on the upper surface. Once the components are aligned with the central axis and the head of the central pin is protruding through the elongate central opening of the locking plate, the user simply slides the locking plate tab(s) to secure and compress the components together. Once the lid and base of the sterilization container are secured, the sterilization container and its contents can be subjected to the sterilization process, e.g. autoclaving.

INDUSTRIAL APPLICABILITY

The filter system of the invention is useful in sterilization containers whenever control and separation between the internal and external environments is desired. The filter system of the invention is especially useful as part of the construction of autoclavable sterilization containers for sterilizing and containing medical devices and instruments in association with medical and surgical procedures.

The invention has been described with reference to various specific and preferred embodiments and techniques. It will be understood that reasonable variations and modifications to such specific and preferred embodiments and techniques can be made without departing from the spirit and scope of the invention.

What is claimed is:

1. A filter system for sterilization container having a vented portion comprising a plurality of openings, said filter system comprising:
   a first filter retention plate comprising a plurality of openings;
   a second protective plate comprising a plurality of openings;
      wherein said first filter retention plate and second protective plate are structured so that the openings thereof and said openings of said vented portion are arranged to permit substantially unobstructed movement of air across said filter while forming a barrier to transverse physical perforation of said filter, said openings maintaining such barrier irrespective of rotational positioning of said plates relative to a central axis.

* * * * *